United States Patent [19]

Eshel et al.

[11] Patent Number: 4,813,429

[45] Date of Patent: Mar. 21, 1989

[54] CATHETER AND PROBE

[75] Inventors: Uzi Eshel, Herzlia; Avigdor Lev, Petach Tikva, both of Israel

[73] Assignee: Biodan Medical Systems Ltd., Rehovot, Israel

[21] Appl. No.: 46,193

[22] Filed: May 5, 1987

[30] Foreign Application Priority Data

May 12, 1986 [IL] Israel .................................. 78756

[51] Int. Cl.⁴ ............................................. A61B 10/00
[52] U.S. Cl. .................................. 128/736; 128/653;
128/804; 604/43
[58] Field of Search ............... 128/642, 736, 653, 804,
128/399, 401; 604/43, 45

[56] References Cited

U.S. PATENT DOCUMENTS

| | | | |
|---|---|---|---|
| 4,311,154 | 1/1982 | Sterzer et al. | 128/804 |
| 4,369,795 | 1/1983 | Bicher et al. | 128/736 |
| 4,476,872 | 10/1984 | Perlin | 128/736 X |
| 4,497,324 | 2/1985 | Sullivan et al. | 128/736 |
| 4,601,296 | 7/1986 | Yerushalmi | 128/804 |
| 4,638,813 | 1/1987 | Turner | 128/804 |

FOREIGN PATENT DOCUMENTS 2566905  1/1986  France .............................. 128/736

*Primary Examiner*—Lee S. Cohen
*Attorney, Agent, or Firm*—Benjamin J. Barish

[57] ABSTRACT

A catheter for insertion into a body cavity, comprises a tubular shaft formed with a passageway extending longitudinally therethrough closed at one end and open at the opposite end and a probe removably received within the passageway through its open end. The probe includes a temperature sensor for sensing the heat produced by a heating applicator applied to an adjacent area of the body. The heating applicator includes a microwave antenna producing an electromagnetic field for heating the body tissue adjacent to the body cavity, and the sensor including an electromagnetic field detector for detecting the peak of the electromagnetic field produced by the applicator antenna.

7 Claims, 3 Drawing Sheets

FIG 3
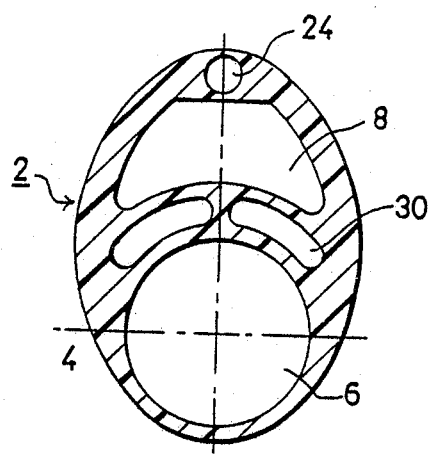
FIG 4
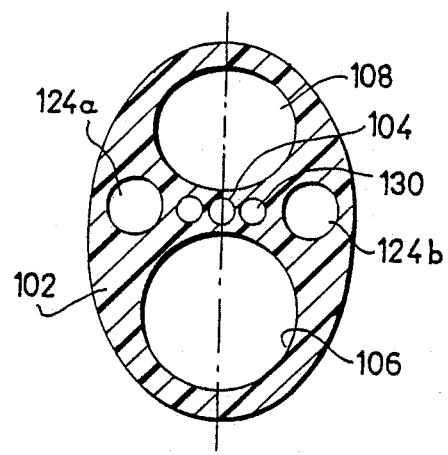
FIG. 5
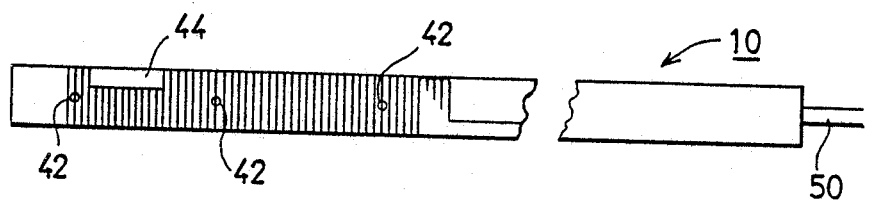
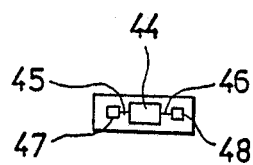
FIG. 6
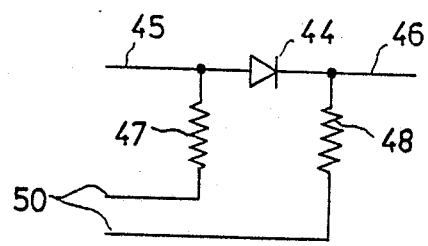
FIG. 7

CATHETER AND PROBE

BACKGROUND OF THE INVENTION

The present invention relates to a catheter and probe, and particularly to a catheter and probe for insertion into a body cavity in order to properly locate an applicator inserted into an adjacent body cavity. The invention is especially useful with applicators inserted into a patient's rectum for applying a hyperthermia treatment to the prostate, and is therefore described below with respect to this application.

Hyperthermia is a recognized technique for various therapeutic treatments by the application of heat. One known type of applicator includes a microwave antenna which is inserted into the patient to heat the prostate. An improved applicator of this type is described in our companion application No. 07/046,195 filed the same date as this application. A problem involved in the use of such applicators, however, is to precisely locate the microwave antenna so as to maximize the effectiveness of the hyperthermia treatment. Another problem is to precisely measure the temperature at the treated site.

An object of the present invention is to provide a catheter and also a probe particularly useful for precisely locating a heating applicator inserted into a body cavity, and also for precisely measuring the temperature at the treated site. The catheter and probe of the present application are particularly useful with the microwave heating applicator described in the above-cited companion application.

BRIEF SUMMARY OF THE INVENTION

According to the present invention, there is provided a catheter for precisely locating an applicator antenna when inserted through a patient's rectum for subjecting the patient's prostate to a hyperthermia treatment by producing an electromagnetic filed, the catheter comprising: a tubular shaft insertable via the urethra of the patient through the prostate and into the bladder; a balloon carried at one end of the shaft and inflatable by a fluid for anchoring the respective end of the shaft in the bladder; the shaft being formed with first and second passageways extending longitudinally therethrough to the one end; a probe received in the first passageway comprising a microwave receiving antenna for precisely locating the peak of the electromagnetic field produced by the applicator antenna, when inserted into the rectum, with respect to the prostate; the second passageway being open at the one end of the tubular shaft inserted into the bladder for conducting a draining and/or irrigating liquid from or to the bladder.

In the described preferred embodiment, the probe further includes a temperature sensor for measuring the temperature of the tissues adjacent the prostate to be treated.

According to a further feature, the first and second passageways are separated by a partition wall formed with a plurality of air openings therethrough to thermally insulate the probe from the draining or irrigating liquid passing through the second passageway.

Further features and advantages of the invention will be apparent from the description below.

BREIF DESCRIPTION OF THE DRAWINGS

The invention is herein described, by way of example only, with reference to the accompanying drawings, wherein:

FIG. 3 is an enlarged transverse-sectional view along lines III—III of FIG. 2;

FIG. 4 is a view, corresponding to that of FIG. 3, but illustrating a modification in the construction of the catheter;

FIG. 5 is an end-elevational view illustrating the probe in the catheter assembly of FIG. 1;

FIG. 6 is a fragmentary view illustrating a part of the probe of FIG. 5;

FIG. 7 is a schematic diagram illustrating the equivalent electrical circuit in the part of the probe illustrated in FIG. 6.

DESCRIPTION OF A PREFERRED EMBODIMENT

Figure 1:
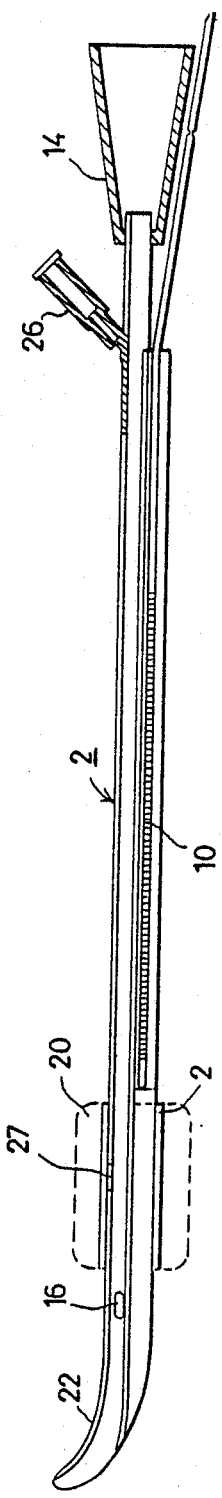
FIG. 1 is an end-elevational view, partly in section, illustrating one form of catheter assembly in accordance with the invention with the balloon inflated.

The catheter assembly illustrated in FIG. 1 is intended to be used for precisely locating a microwave-field generating applicator, such as described in the above-cited companion application, inserted into the patient's rectum for purposes of rendering a hyperthermia treatment to the patient's prostate. The primary purpose of the catheter assembly illustrated in FIG. 1 is to accomodate a probe inserted with the catheter into the patient's urethra, in order to precisely locate the applicator with respect to the patient's prostate, and also to precisely measure the temperature at the treated site. The patient's bladder is used for locating the catheter, and thereby the applicator, and therefore the catheter may also be used for draining and/or irrigating the bladder.

The catheter illustrated in FIG. 1 comprises a catheter shaft 2 of flexible plastic material of hollow oval shape in section, and formed with a partition wall 4 (FIG. 3) extending for substantially its complete length. Partition wall 4 divides the interior of the catheter shaft into a first passageway 6 and a second passageway 8 both closed at one end and open at the opposite end.

Figure 2:
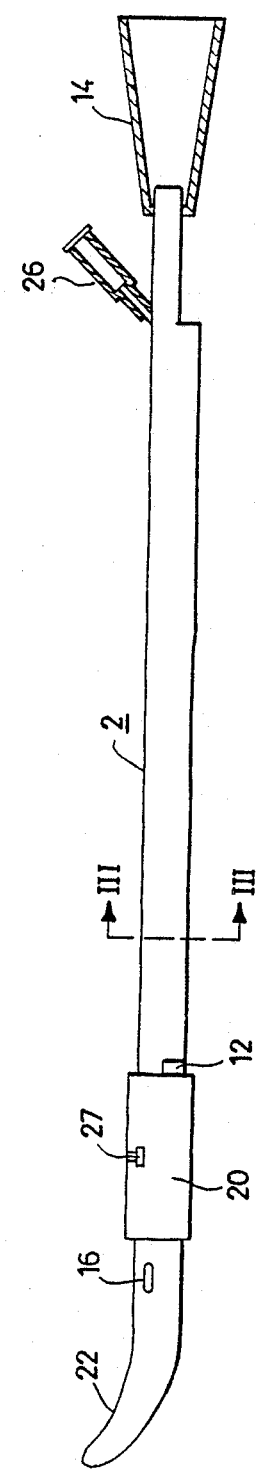
FIG. 2 is a side elevational view, partly in section, illustrating only the catheter jacket.

Passageway 6 is used for receiving a probe 10 (FIGS. 1 and 5). Probe 10 is inserted via the open end of passageway 6 to a limit element 12 (FIG. 2) inserted into the passageway at the closed end thereof for precisely positioning the probe within the passageway.

Passageway 8 is used for conducting the liquid draining from the patient's bladder, and/or the liquid applied to the patient's bladder to irrigate it. For this purpose, the open end of the catheter shaft is provided with an end fitting 14 communicating with passageway 8, and the closed end of the catheter shaft is formed with an opening 16 also communicating with passagewy 8. Thus, when the catheter is used for draining the bladder, the draining liquid enters passageway 8 via opening 16 and exits from the catheter via end fitting 14; and when the catheter is used for irrigating the bladder, the irrigating liquid is applied to the bladder via end fitting 14, passageway 8 and opening 16.

Catheter 2 further includes a balloon 20 fixed to and extending around the closed end of the shaft 2 for anchoring the catheter in the bladder. Such balloons are commonly constructed as a part of an end fitting 22 of various types according to the particular requirements of the catheter. In the example illustrated in FIGS. 1 and 2, end fitting 22 is of the Tiemann type, although it will be appreciated that the other types could also be used.

For purposes of inflating balloon 20, the catheter shaft 2 is formed with a further passageway 24 extending from an end fitting 26 at the open end of the catheter shaft. Passageway 24 is used for applying air or water to inflate the balloon and extends to an outlet opening 27 at the closed end of the catheter shaft communicating with the balloon.

According to an important feature of the catheter illustrated in the drawings, the partition wall 4 separating passageway 6 receiving the probe 10, from passageway 8 through which the draining or irrigating liquid flows, is formed with one or more air openings 30 therethrough for substantially the complete length of the catheter shaft. FIG. 3 illustrates the partition wall formed with two elongated openings 30. Such air openings increase the thermal insulation properties of the partition wall 4, and thereby decrease the influence that the irrigating or draining liquid flowing through passageway 8 will have on the temperature measurements of the probe 10 received within passageway 6.

FIG. 4 illustrates a modification in the construction of the catheter shaft. Thus, the catheter shaft illustrated in FIG. 4, therein designated 102, is of oval shape as in FIG. 3 and includes a partition wall 104 separating the probe-receiving passageway 106 from the liquid passageway 108. In addition, partition wall 104 is formed with air openings 130 therethrough to increase the thermal insulation properties of the partition wall in order to minimize the effects of the liquid passing through passageway 106 on the temperature measurements of the probe received within passageway 108.

In the construction of the catheter shaft illustrated in FIG. 4, however, the two passageways 106 and 108 are both of circular cross-section, passageway 108 being of slightly larger diameter for receiving the probe. In addition, instead of having a single passageway for inflating the balloon, in the construction illustrated in FIG. 4 there are two such passageways 124a, 124b, both formed through partition wall 104 on opposite sides of air passageways 130. One of these passageways may be used for inflating and deflating the balloon, while the other may be used for delivering drugs, draining, irrigating, or the like.

The probe received witin passageway 106 is more particularly illustrated in FIG. 5. It comprises one or more temperature-measuring thermocouples 42 for measuring the temperature at the site heated by the applicator inserted into the patient's rectum, and a diode 44 for sensing the peak of the microwave field generated by the applicator.

Diode 44 defines a dipole antenna with a pair of electrical leads 45, 46, projecting from its opposite sides, which leads are connected to electrical resistors 47, 48. The diode converts the received energy of the microwave field to a voltage which is outputted from the probe via electrical conductors 50. This output voltage may therefore be used for detecting the peak of the microwave field generated by the applicator.

Thermocouples 42 measure the temperature, and output an electrical voltage in response to the measured temperature. In the illustrated arrangement, there are three thermocouples in side-by-side relationship so as to measure the temperature at three regions along the length of the probe. The thermocouples produce voltages proportional to the measured temperature, which voltages are outputted by electrical conductors 50.

The conductors 50 to the thermocouples 42 and diode 44 are disposed in the form of a spiral extending circumferentially of the probe 10, and thereby also of the catheter shaft 2. The spiral form of the electrical conductors increases the characteristic impedance of these conductors and therefore the DC electrical signals outputted from the diode and thermocouples via these electrical conductors are less influenced by the electromagnetic field, and also influence such field to a lesser extent.

FIG. 8 illustrates the manner of using the catheter and probe described above, and generally designated 60 in FIG. 8, inserted into the urethra of a patient in order to precisely locate a probe 70 inserted into the rectum of the patient for applying a hyperthermia treatment to the patient's prostate 72. A number of applicators are known for rendering this type of treatment, a preferred applicator being that described in our above-cited companion Patent Application.

Figure 8:
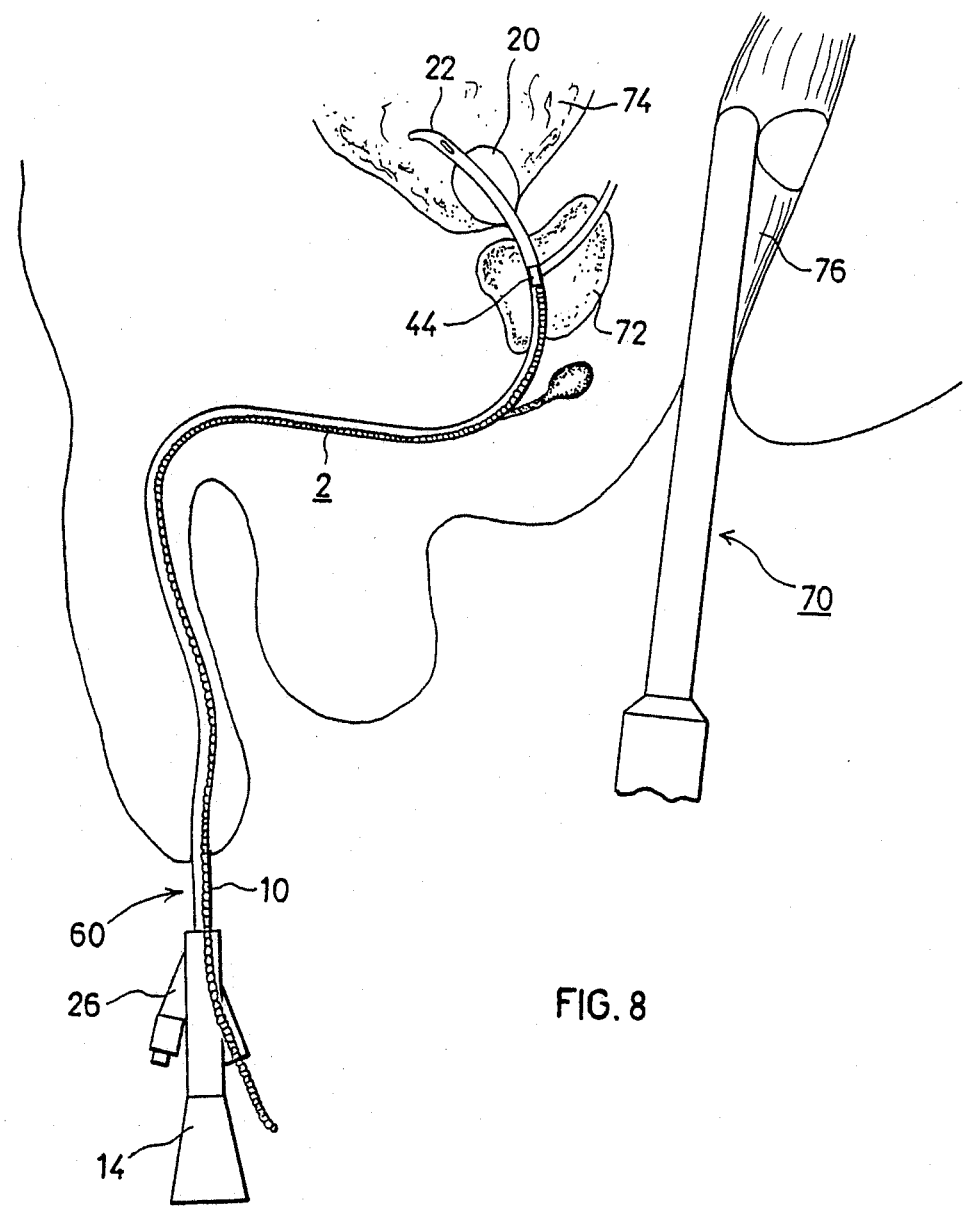
FIG. 8 illustrates the manner of using the catheter and probe of FIGS. 1–7 with a microwave-type heating applicator such as described in the above-cited companion patent application.

The probe 10 may be inserted into the catheter jacket 2 before or after the catheter has been inserted into the patient. The catheter is inserted with the balloon deflated and is advanced along the urethra, through the prostate 72, and into the bladder 74. Balloon 20 within the patient's bladder is inflated by introducing water (or air) via inlet fitting 26. The catheter is then slightly withdrawn until the inflated balloon 20 limits against the neck of the bladder, as shown in FIG. 8.

The distance between diode 44 of the probe 10, and balloon 20 of the catheter shaft 2, is such that when balloon 20 limits against the neck of the bladder, the diode 44 is located substantially centrally of the patient's prostate 72. This is to be the location of the peak of the electromagnetic field produced by the applicator 70.

The applicator 70 may then be inserted into the patient's rectum 76 while a small amount of electrical energy is applied to the applicator, and the applicator is moved in the rectum until a maximum reading is produced by diode 44 of the probe 10. This indicates that the applicator is precisely located such that the peak of the electromagnetic field produced by the applicator passes through the location of diode 44 within the prostate 72.

The applicator 70 may then be fully energized to produce the electromagnetic field for rendering the hyperthermia treatment to the prostate 72, and the thermocouples 42 carried by the probe 10 may be used for measuring the temperature at their respective locations along the length of the probe.

As mentioned above, the electrical conductors 50 to the thermocouples 42 and diode 44 are disposed in a spirally coiled configuration, such that their characteristic impedance is increased, thereby making them substantially insensitive to the electromagnetic field produced by the applicator. The DC readings outputted by the electrical conductors from the diode 44 and the thermocouples 42 will be substantially immune from the electromagnetic field produced by the applicator 70.

It will thus be seen that the use of the catheter and probe as described above with the applicator 70, for rendering a hyperthermia treatment to the patient's prostate, enables the applicator to be precisely positioned with respect to the patient's prostate in order to produce the maximum heating effect on the prostate and also to provide precise measurements of the temperature of the tissues at the site heated by the applicator. In addition, since the partition wall between the passageway receiving the probe (e.g. passageway 6 in FIG. 3) and the passageway (e.g. 8) for conducting the liquid draining from the bladder and/or irrigating the bladder, is provided with air openings (30, FIG. 3), the thermal insulation produced by the partition wall is increased so as to minimize the influence of the draining and/or irrigating liquid on the output readings produce from the probe.

While the invention has been described with respect to a preferred embodiment wherein the catheter and probe are used for precisely positioning a heating applicator applied to the patient's rectum, and for providing precise measurements of the heat so produced, it will be appreciated that the invention could be used in other applications for precisely positioning an applicator in another body opening of a patient, such as a blood vessel, and/or for providing precise measurements of the heat or other condition produced by such an applicator. Many other variations, modifications and applications of the invention will be apparent.

What is claimed is:

1. A catheter for precisely locating an applicator antenna when inserted through a patient's rectum for subjecting the patient's prostate to a hyperthermia treatment by producing an electromagnetic field, said catheter comprising:
    a tubular shaft insertable via the urethra of the patient through the prostate and into the bladder;
    a balloon carried at one end of said shaft and inflatable by a fluid for anchoring the respective end of the shaft in the bladder;
    said shaft being formed with first and second passageways extending longitudinally therethrough to said one end;
    a probe received in said first passageway comprising a microwave receiving antenna for precisely locating the peak of the electromagnetic field produced by the applicator antenna, when inserted into the rectum, with respect to the prostate;
    said second passageway being open at said one end of the tubular shaft inserted into the bladder for conducting a draining and/or irrigating liquid from or to the bladder.

2. The catheter according to claim 1, wherein said probe further includes a temperature sensor for sensing the temperature of the tissue adjacent the prostate to be treated.

3. The catheter according to claim 2, wherein said receiving antenna and temperature sensor include electrical conductors extending spirally around said probe.

4. The catheter according to claim 1, wherein said tubular shaft includes a third passageway extending longitudinally therethrough to said balloon for conducting the fluid to inflate the balloon.

5. The catheter according to claim 1, wherein said first and second passageways are separated by a partition wall formed with a plurality of air openings extending longitudinally of the shaft to thermally insulate the probe from the draining or irrigating liquid passing through said second passageway.

6. a catheter for insertion into the urethra of a patient, said catheter comprising a flexible tubular shaft formed with a first passageway extending longitudinally therethrough and having a closed end and an opposite open end for receiving a probe having a temperature sensing device; and a second passageway formed longitudinally therethrough and having openings at its opposite ends for conducting a draining and/or irrigating liquid from or to the patient's bladder; said two passageways being separated by a partition wall formed with a plurality of air openings extending longitudinally of the shaft to thermally insulate the probe in said first passageway from the draining or irrigating liquid passing through said second passageway.

7. The catheter according to claim 6, further including a balloon attached to said shaft and inflatable by a fluid for anchoring the catheter shaft to the patient's bladder.

* * * * *